United States Patent [19]

Samour et al.

[11] Patent Number: 4,861,764
[45] Date of Patent: Aug. 29, 1989

[54] PERCUTANEOUS ABSORPTION ENHANCERS, COMPOSITIONS CONTAINING SAME AND METHOD OF USE

[75] Inventors: Carlos M. Samour, Wellesley; Stefanos Daskalakis, Lawrence, both of Mass.

[73] Assignee: Macro Chem. Corp., Billerica, Mass.

[21] Appl. No.: 931,653

[22] Filed: Nov. 17, 1986

[51] Int. Cl.$^4$ .............................................. A61K 31/56
[52] U.S. Cl. .................... 514/177; 514/263; 514/415; 514/452; 514/467; 514/947
[58] Field of Search ............... 514/452, 467, 947, 177, 514/263, 415

[56] References Cited

U.S. PATENT DOCUMENTS

| | | | |
|---|---|---|---|
| 4,012,520 | 3/1977 | Youngdale | 514/467 |
| 4,085,222 | 4/1978 | Rhodes et al. | 514/452 |
| 4,085,223 | 4/1978 | Carissimi et al. | 514/467 |
| 4,557,934 | 12/1985 | Cooper | 424/128 |

*Primary Examiner*—Leonard Schenkman
*Attorney, Agent, or Firm*—N. Blumenkopf

[57] ABSTRACT

Novel 1,3-dioxolanes (1,3-dioxyacyclopentanes) are provided along with new 1,3-dioxolanes (1,3-dioxacyclopentanes) compositions which are useful in enhancing the absorption of therapeutic agents through the skin of humans and animals. The method for enhancing skin penetration of therapeutic agents using 1,3-dioxacycloalkanes is also described.

The preferred compounds are 1,3-dioxolanes (1,3-dioxacyclopentanes) and 1,3-dioxanes (1,3-dioxacyclohexanes). The preferred compounds have the formula:

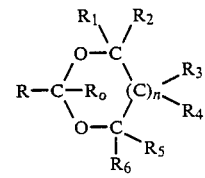

wherein R, $R_0$, $R_1$, $R_2$, $R_3$, $R_4$, $R_5$ and $R_6$ are each independently selected from hydrogen and $C_1$ to $C_{18}$ aliphatic groups, preferably alkyl, alkenyl, and the halo, hydroxy, carboxy, carboxamide and carboalkoxy substituted forms thereof, with at least one of said R's an alkyl or alkenyl group of $C_4$ to $C_{18}$ and $n=0$ or 1; the total number of carbon atoms in all of said R groups being no more than 40, and preferably less than 20 and not more than 1 thereof containing 18 or more carbon atoms.

17 Claims, No Drawings

PERCUTANEOUS ABSORPTION ENHANCERS, COMPOSITIONS CONTAINING SAME AND METHOD OF USE

BACKGROUND OF THE INVENTION

The present invention relates to a method for enhancing skin penetration of therapeutic agents utilizing certain 1,3-dioxacyclopentanes and 1,3-dioxacyclohexanes and compositions containing such compounds as well as to new penetration enhancing compounds within these chemical classifications.

The desirability, of the delivery of physiologically active agents through the skin, i.e. transdermally, as opposed to other methods of parenteral administration or via the digestive system is based on many factors. The large surface area of the skin (over 3,000 square inches for the average adult) and the large circulatory (about one-third of total body blood) and lymphatic networks available near the skin, the generally non-invasive nature of topical applications and their delivery through the skin, the convenience, the safety, the potential greater control of delivered agents, and the minimal side effects are just some of the advantages seen for this technique.

While not every and all agents may be suitable for transdermal delivery because of local irritation, allergic reactions, etc., most are indicated as suitable but, unfortunately, the greatest problem is overcoming the general barrier to drug penetration (or indeed to any material) of the skin. A drug must pass through the outer layer of skin or epidermis and into the dermis layer before being absorbed into the blood stream. The epidermis comprises two main parts, the stratum corneum and the stratum germinativum. The stratum corneum forms the outermost layer of the epidermis and consists of many stratified layers of compacted, flattened, keratinized cells which have lost their nuclei. This outmost layer serves as a physical barrier to light, heat, microorganisms and most chemical agents. In addition, it behaves as a primary barrier to percutaneous absorption. Because of the barrier effect of the skin, it has heretofore only been possible to deliver drugs that are "low-dose" drugs, in the range of 10 mg/day or less, or those of low molecular weight. In addition they have to have the proper lipophilic-hydrophilic balance to permit adequate absorption. It was recognized as early as the beginning of this century that lipid-soluble substances, such as nonelectrolytes have a comparatively greater skin permeability than water-soluble substances, such as electrolytes.

The phenomenon of percutaneous absorption or transdermal permeation can be viewed as a composite of a series of steps in sequence, that is, adsorption of a penetrant molecule onto the surface layers of stratum corneum, diffusion through it and through the viable epidermis, and finally through the papillary dermis and into the microcirculation. The great diffusional resistance of stratum corneum has been demonstrated in a comparative absorption of drugs, like hydrocortisone. The mucous membranes in the rectal and vaginal regions permit the absorption of 26–29% of the steroid applied, while less than 2% of the applied dose is absorbed through the skin.

Compounds which are known or reported to enhance the transdermal delivery of drugs include dimethyl sulfoxide (DMSO), polyethylene glycol monolaurate, alkyl lactams, and long-chain amides. Prior art patents of relevance to penetrating enhancers for physiologically active agents include U.S. Pat. Nos. 3,551,554 which describes dimethyl sulfoxide; 3,989,816 discloses 1-substituted azacycloheptane-2-one; U.S. Pat. No. 4,132,781 discloses a topical antibiotic plus 2-pyrrolidone or an n-lower alkyl-2-pyrrolidone, U.S. Pat. No. 4,017,641 also describes 2-pyrrolidone but with propylene glycol; others of interest are U.S. Pat. Nos. 3,903,256; 4,343,798; 4,046,886; 3,934,013; 4,070,462; 4,130,643; 4,130,667; 4,289,764; 4,070,462; 3,527,864; 3,535,422, 3,598,123, 3,952,099, 4,379,454, 4,286,592; 4,299,826; 4,314,557; 4,343,798; 4,335,115; 3,598,122; 4,405,616, 3,896,238 and 3,472,931. Attention is also directed to U.S. Pat. No. 4,557,934 and this patent as well as the others previously mentioned are hereby incorporated in their entirety by reference thereto. None of the references cited heretofore discloses any 1,3 dioxolane or 1,3 dioxane and especially any of the substituted types previously mentioned and hereinafter described for use as percutaneous absorption enhancers for physiologically active substances.

SUMMARY OF THE INVENTION

The present invention relates to a class of compounds which are effective in enhancing the transport of a large number of higher-dose, poorly-absorbed drugs through the skin.

The compounds which are provided by and for use in this invention are substituted-1,3-dioxacyclopentanes and substituted 1,3-dioxacylcohexanes.

The compounds have the general formula:

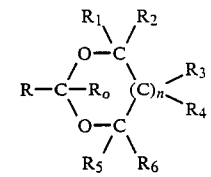

wherein R, $R_0$, $R_1$, $R_2$, $R_3$, $R_4$, $R_5$ and $R_6$ are each independently selected from hydrogen and $C_1$ to $C_{18}$ aliphatic groups, preferably alkyl, alkenyl, and the halo, hydroxy, carboxy, carboxamide and carboalkoxy substituted forms thereof, with at least one of said R's an alkyl or alkenyl group of $C_4$ to $C_{18}$ and n=0 or 1; the total number of number of carbon atoms in all of said R groups being no more than 40 and preferably not more than 1 thereof containing 18 or more carbon atoms.

Preferred compounds with the general formula (I) where R is $C_4$ to $C_{18}$ and preferably $C_6$ to $C_{12}$ and more preferably $C_7$ to $C_{10}$. Another preferred class are the cyclopentanes (i.e. dioxolanes) in which R & $R_0$ are hydrogen and one of $R_1$, $R_2$, $R_5$ & $R_6$ is $C_4$ to $C_{18}$, preferably $C_6$ to $C_{12}$ and more preferably $C_7$ to $C_{10}$. The preferred moieties for the R groups are alkyl, alkenyl, carboalkoxy

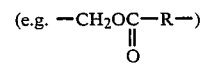

or —$CH_2OR$.

General formula representing most preferred enhancers are the following:

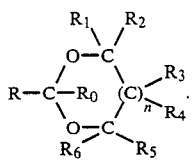

where R is $C_4$ to $C_{18}$, preferably $C_6$ to $C_{12}$ most preferably $C_7$ to $C_{10}$ and the other R groups are lower moieties ($C_1$ to $C_4$) or any of the other groups such as hydrogen, halo, carboxy, hydroxy, amide and the like, and $n=0$ or 1; and

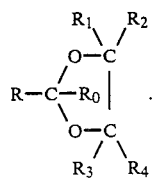

where one of the R groups is $C_4$ to $C_{18}$, preferably $C_6$ to $C_{12}$ and more preferably $C_7$ to $C_{10}$ and the others are as in formula II; and

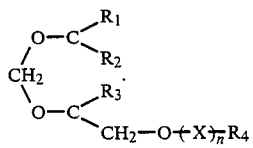

where $R_4$ is $C_4$ to $C_{18}$, preferably $C_6$ to $C_{12}$ and more preferably $C_7$ to $C_{10}$ and $R_1$, $R_2$ and $R_3$ are again as the others in formulas II and III, $n=0$ or 1 and when $n=1$, X is carbonyl

In formulas II and III, it is preferred that $R_o$ is hydrogen. In Formula III it is also preferred that R is also hydrogen.

The compounds contemplated herein may be applied in conjunction with any agent it is desired to transdermally administer to humans and animals, as in admixture therewith. It is also often desirable to pretreat the skin immediately before (e.g. for several minutes or longer i.e. 15 minutes, 30 minutes, one hour, etc.) or after, e.g. in immediate sequence or after 15 minutes, or 30 minutes, or one hour, or 10 hours or 24 hours etc. The dioxane or dioxolane with or without therapeutic agent or other additives may be incorporated into any suitable substrate as by coating, or impregnation. It may be admixed with a hydrophilic or hydrophobic material and in this form coated onto a suitable substrate, or formed into a film (e.g. using a film - forming hydrophilic or hydrophobic resin such as polyethylene, nylon, polyester, polyurethane, hydrolyzed (e.g. 85%) polyvinyl acetate, cellolose acetate, regenerated cellulose, etc.) and used as a self-sustained film or laminated or otherwise joined to another substrate e.g. paper, metal, non-woven (resin or spun-bonded) fabrics, woven fabrics (e.g. cotton, rayon, nylon, polyester and the like). The enhancer alone or with medicant and/or additives may be dissolved or dispersed in one of the foregoing thermoplastic resins or in any other as well and melt spun or calendored or molded into and desired shape or structure. A very useful substrate for the enhancer per se or in combination with a physiologically active agent is in a pressure-sensitive adhesive mostly generally in association with any carrier base (e.g. plastic, paper, cloth, metal, foil, etc.).

It is of courses obvious that many of the usual adjuvants commonly or otherwise utilized and/or administered with the selected physiologically active agent can be employed in the various compositions, articles and processes contemplated and described herein.

Such adjuvants include, inter alia, solvents such as water, ethanol, etc., lipid materials, coloring agents, fragrances, anti-oxidants, thickening agents, ultraoxidants, thickening agents, ultra-violet light stabilizers preservatives, and others conventional in such compositions.

EXAMPLE I

Preparation of 2-n-pentyl-1,3 dioxolane (1)

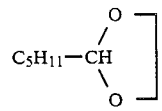

30 g (0.29 mole) of hexanol, 31 g (0.5 mol) of ethylene glycol, 100 mg of p-toluenesulfonic acid (p-Ts) in 100 ml of benzene are placed in 250 ml round-bottomed flask equipped with a Dean-Stark trap, a condenser and a mechanical stirrer. The mixture is heated to reflux until no more water has separated from the benzene phase. The mixture is then cooled to room temperature, washed with 100 ml of 5% sodium bicarbonate, 100 ml of saturated NaCl solution, and finally water. The solution is dried over sodium sulfate. After removing the solvent, the oil is fractionated. A yield of 19.6 g of colorless oil (46%) is obtaind $n_D^{20} = 1.4554$.

EXAMPLE II

Preparation of 2-n-heptyl-1,3 dioxolane (2)

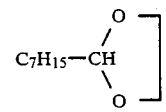

Following procedure given for compound I, from 30 g (0.23 mole) of octyl aldehyde, 31 g (0.5 mole) of ethylene glycol, 100 mg of p-Ts. in 70 ml of benzene there is obtained 20.5g (50.9%) of a colorless oil. $n_D^{20} = 1.4336$.

EXAMPLE III

Preparation of 2-n-nonyl-1,3 dioxolane (3)

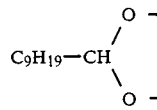

Following example I from 78.77 g of decylaldehyde (0.5 mole), 37.22 g (0.6 mole) of ethyleneglycol, 0.5 g of p-toluenesulfonic acid in 100 ml toluene there is obtained 78 g (77.4%) of a colorless product; b.p. 80°–81° C./0.5 mm. $n_D^{20} = 1.4392$.

EXAMPLE IV

Preparation of 2-n-undecyl-1,3 dioxolane

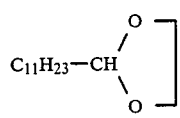

Following example I, 45.56 g (0.25 mole) of dodecyl aldehyde, 17.85 g (0.288 mole) of ethylene glycol, 0.02 g of para-toluenesulfonic acid in 140 ml toluene are reacted to obtain 30 g (55%) of a colorless product; b.p. 112°–116°/1.5 mm. $n_D^{20} = 1.9999$.

EXAMPLE V

Preparation of pentylene-1,5-bis-1,3 dioxolane (5)

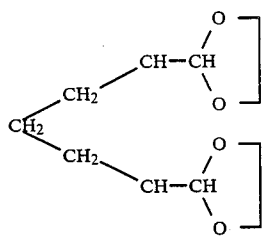

Following procedure given for compound 1, 32 g (0.31 mole) of glutaraldehyde, 52.01 g (0.83 mole) of ethylene glycol, 200 mg. of p-Ts. in 150 ml of benzene are reacted to yield 46.03 g (67%) of a colorless oil having an $n_D^{20} = 1.4559$. b.p. = 0.1 mm/78°–82° C.

EXAMPLE VI

Preparation of 2-(2',6'-dimethyl-2',6'-heptadienyl)-1,3 dioxolane (6)

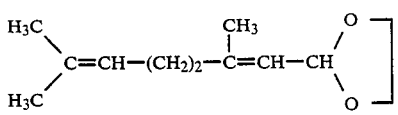

Following example I, from 50 g (0.32 mole) of citral, 24.8 g (0.4 mole) ethylenecylycol, 0.02 g of p-toluenesulfonic acid in 75 ml benzene is obtained 18.2 g of a light yellow oil; $n_D^{20} = 1.4940$; b.p. = 0.5 mm/34°–36° C.

EXAMPLE VII

Preparation of 2-(2',6'-dimethyl-2'heptaenyl)-1,3 dioxolane (7)

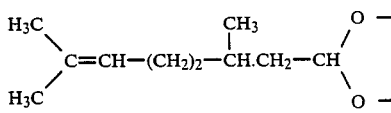

30.58 g of 80% citronellal (0.158 mole) is placed in a 500 ml flask equipped with a distilling receiver, condenser equipped with a drying tube and a magnetic stirrer. 14.59 g of ethylene glycol (0.23 mole) and 0.02 g of p-toluenesulfonic acid in 100 ml of dry benzene is then added and the mixture is heated to reflux under stirring until no more water has separated in the distiling receiver (about 6 hours). Upon completion of the reaction the mixture is washed with 2×10 ml (5%) sodium bicarbonate solution, water and dried over sodium sulfate. The reaction mixture is filtered and the filtrate is concentrated to a yellow oil. Distillation yields 17.57 g (41%) of a colorless product; b.p. 65°–70° C./0.5 mm. $n_D^{20} = 1.4645$.

EXAMPLE VIII

Preparation of 2-n-nonyl-5-chloromethyl-1,3 dioxolane (8)

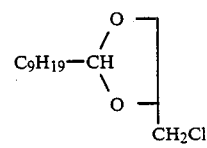

Following procedure given for compound I, from 24.95 g (0.16 mole) of decyl-aldehyde, 17.6 g (0.16 mole) of 3-chloro-1,2-propanediol, 0.2 g of p-Ts. in 100 ml of toluene there is obtained 30.49 g of a colorless oil (77%); b.p. = 0.14 mm/91°–100° C. $n_D^{20} = 1.4533$.

EXAMPLE IX

Preparation of 2-(2',6'-dimethyl-2'-heptaenyl)-1,3 dioxolane (9)

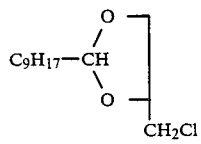

Following procedure given for compound I, from 15 g (0.097 mole) of 3-chloro-1,2-propanediol, 10 g (0.06 mole) of citronellal, 150 mg p-Ts. in 75 ml of benzene there is obtained 12.56 g of a crude product (oil).

EXAMPLE X

Preparation of 2-(2',6'-dimethyl-2',6'-heptadienyl)-5-chloromethyl-1,3 dioxolane

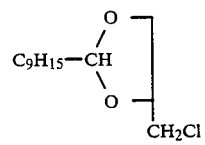

Following procedure given for compound I from 12.77 g (0.08 mole) of citral, 10 g (0.09 mole) of 3-chloro-1,2 propadiol, 60 mg of p-Ts in 50 ml of benzene there is obtained 10.7 g of raw oil (54.7%).

EXAMPLE XI

Preparation of 2-(2',6'-dimethyl-2',6'-heptadienyl)-5-hydroxymethyl 1,3-dioxolane

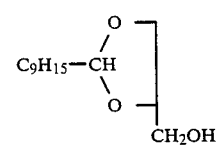

Following example I 51.4 g (0.33 mole) of citral 46 g (0.5 mole) of glycerol and 0.04 g of p-toluenesulfonic acid in 150 ml benzene are reacted to give 31.45 g of a colorless oil (41.11%) $n_D^{20}=1.4963$.

EXAMPLE XII

Preparation of 2-(2′,6′-dimethyl-2′-heptaenyl)-5-hydroxymethyl-1,3 dioxolane

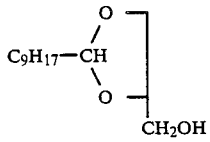

Following procedure given for product I, from 27.62 g (0.3 mole) of glycerol, 17.2 ml of citronellal (0.1 mole), 400 mg of p-Ts in 150 ml toluene there is obtained 9.69 g of an oil.

EXAMPLE XIII

Preparation of 2-n-nonyl-1,3 dioxane

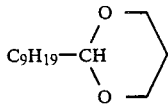

Following example I from 78.77 g of decylaldehyde (0.5 mole), 45.65 g (0.6 mole) of 1,3 propandiol 0.5 g of p-toluenesulfonic acid in 100 ml toluene are reacted to obtain 67.69 (62.65%) of a colorless product with a b.p. 70°–74° C./0.1 mm. Hg and an $n_D^{20}=1.4448$.

EXAMPLE XIV

Preparation of 2-n-undecyl-1,3 dioxane

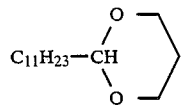

Following procedure given for product I from 11.19 g (0.064 mol) of dodecylaldehyde, 7.5 g (0.098 mole) of 1,3 propandiol, 50 mg. of p-Ts in 50 ml of abenzene there is obtained 7.46 g (48%) of a colorless oil which with an $n_D^{20}=1.4477$ and a b.p.=0.065 mm/89° C.

EXAMPLE XV

Preparation of 2-(2′,6′-dimethyl-2′-heptaenyl)1,3 dioxane

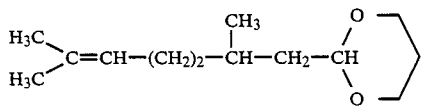

10 g of 80% citronellal (64 mole) is placed in a 250 ml flask equipped with a distilling receiver, condenser equipped with a drying tube and a magnetic stirrer. 7.5 g of 1,3 propandiol (0.098 mole) and 0.05 g of p-toluenesulfonic acid in 50 l of dry benzene is then added and the mixture is heated to reflux under stirring until no more water separates in the distilling receiver (about 6 hours). Upon completion of the reaction the mixture is washed with 2×10 ml (5%) sodium bicarbonate solution, water and dried over sodium sulfate. The reaction mixture is filtered and the filtrate is concentrated to a yellow oil. Distillation yields 17.57 g (72.6%) of colorless product; b.p. 65°–70° C./0.5 mm. $n_D^{20}=1.4609$.

EXAMPLE XVI

Preparation of 2-(2′,6′-dimethyl-2′,6-heptadienyl)-5-(bis ethylcarboxylate)-1,3 dioxane (18)

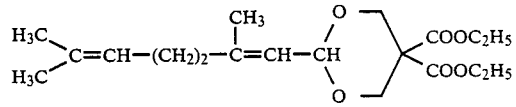

Following procedure given for compound XV from 9.13 g (0.06 mole) of citral, 20 g (0.09 mole) of ethyl (bis-hydroxymethyl)malonate and 0.3 g of p-toluenesulfonic acid in 60 ml of benzene there is obtained a light yellow oil with a b.p.=0.5 mm. Hg/140° C. and an $n_D^{20}=1.4761$.

EXAMPLE XVII

Preparation of 2-n-nonyl-5-(bis ethylcarboxylate)-1,3 dioxane

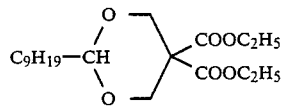

5.2 g of decyl aldehyde (0.33 mole) is placed in a 100 ml flask equipped with a distilling receiver, condenser equipped with a drying tube and magnetic stirrer. 8.53 g (0.0387 mole) of ethyl(bis-hydroxymethyl)malonate and 0.2 g of p-toluenesulfonic acid in 50 ml of dry benzene is then added and the mixture is heated to reflux under stirring until no more water separates in the distilling receiver (about 6 hours). Upon completion of the reaction the mixture is washed with 2×10 ml (5%) sodium bicarbonate solution, water and dried over sodium sulfate. The reaction mixture is filtered and the filtrate is concentrated to a yellow oil. Distillation yields 8.96 g (74.1%) of a colorless product with the following properties: b.p.=0.22 mm Hg/150° C. $n_D^{20}=1.4490$.

EXAMPLE XVIII

Preparation of 2-n-pentyl-5-(bis-ethylcarboxylate)-1,3 dioxane

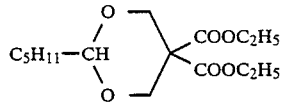

6 g of hexyl aldehyde (0.06 mole) is placed in a 100 ml flask equipped with a distilling receiver, condenser equipped with a drying tube and magnetic stirrer. 20 g (0.09 mole) of ethyl(bis-hydroxymethyl)malonate and 0.2 g of p-toluenesulfonic acid in 60 ml of dry toluene is then added and the mixture is heated to reflux under stirring until no more water separates in the distilling receiver (about 6 hours). Upon completion of the reaction, the mixture is washed with 2×10 ml (5%) sodium bicarbonate solution, water and dried over sodium sulfate. The reaction mixture is filtered and the filtrate is concentrated to a yellow oil. Distillation yields 11.19 g (62%) of colorless product; b.p.=0.2/100°-118° C. $n_D^{20}=1.4453$.

EXAMPLE XIX

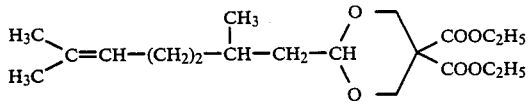

Following procedure given for compound XV from 9.25 g (0.06 mole) of citronellal, 20 g (0.09 mole) of ethyl-(bis-hydroxymethyl)malonate and 0.3 g of p-toluenesulfonic acid in 60 ml of benzene there is obtained 3.5 g of a colorless oil with the following properties: b.p.=0.3 mm/135° C. $n_D^{20}=1.4751$.

The compounds of Examples III, IV, V, VI, VIII XIII, XIV, and XV were tested in vitro using hairless rat skin and a diffusion cell procedure which closely simulates the in vivo situation because the skin is exposed to ambient conditions. The flow-through diffusion cell uses a perfusion of the dermal side of the skin. The sampling is facilitated by an automatic collection of the liquid continuously around the clock. The cells are designed with a water jacket to provide a temperature control and equilibrium of the skin and the dermal liquid.

The general method is as follows. The skin is mounted in the cell and allowed to equilibrate with the environmental conditions for 5 hours (20±1° C.). The water-jacket temperature is 37° C. and the liquid in the dermal compartment is diluted borine albumin in saline water (1.5% w/v). Antibiotics are added in the bathing solution to avoid bacterial development. 500 mg of the test drug in 0.1 ml of ethanol/water (95/5 w/v) mixture are applied on the epidermal surface. After application, the solvent is allowed to evaporate between 1 & 2 hours, and the solid drug deposit remains on the skin. The drug to be tested is a radioactive compound and its absorption flux is monitored after the application of the radioactive mixture by sampling the radioactivity in samples of the dermal solution at hourly intervals during 48 hours. After 24 hours following the drug application 0.1 ml of the enhancer is applied on the treated area.

Following the procedure outlined above the Compound of Example III when tested with progesterone, caffine and indomethacin shows markedly increased skin diffusion when the Example III enhancers is applied to the skin following the drug application. Thus for example during the first 24 hour period (drug alone- no enhancer application) the % indomethacin diffused is 1.47%/cm² while after 48 hours (24 hours after application of enhancer) the % is 12.85%/cm², with progesterone it is found that compound of Example III is 10 times more effective than alcohol or N-dodecyl caprolactam (a reported enhancer).

In a similar vein, compounds of Examples IV, V, VI, VIII, XIII, XIV & XV are found to be outstandingly effective.

In other tests the total % percutaneous absorption after 48 hours (drug first for 24 hours then application of enhancer) shows the following results:

| Composition | Drug | | |
| --- | --- | --- | --- |
| | Progesterone | Caffeine | Indomethaci |
| 1. Drug alone | 4.9 | 7.7 | 1.7 |
| 2. Cpd. Ex VI | 11.98 | 52.4 | 5.3 |
| 3. Cpd. Ex IV | 9.55 | 54.4 | 7.0 |
| 4. Cpd. Ex III | 14.3 | 47.6 | 14.3 |
| 5. Cpd. Ex VIII | 11.0 | 11.4 | 1.8 |

We claim:
1. A therapeutic composition suitable for transdermal administration to humans and animals comprising a therapeutically effective amount of a physiologically active agent and as a penetration enhancer an effective amount of a pharmaceutically acceptable 1,3-di oxacyclopentane or 1,3-dioxacyclohexane containing at least one aliphatic group having 4 to 18 carbon atoms.

2. A therapeutic composition suitable for transdermal administration to humans and animals comprising a physiologically active agent and an effective skin penetration enhancer as defined in claim 1 having the formula:

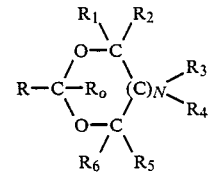

wherein R, $R_0$, $R_1$, $R_2$, $R_3$, $R_4$, $R_5$, and $R_6$ are each independently selected from hydrogen and $C_1$ and $C_{18}$ aliphatic groups, with at least one of said R's being an alkyl or alkenyl group of $C_4$ to $C_8$, and n=0 or 1; the total number of carbon atoms in all of said R groups being no more than 40, and not more than 1 thereof containing 18 or more carbon atoms.

3. A therapeutic composition as in claim 2 where n=0.

4. A therapeutic composition as in claim 2 where R in undecyl.

5. A therapeutic composition as in claim 2 where n=1.

6. A therapeutic composition as in claim 3 wherein R=$C_5$ to $C_{10}$ aliphatic moiety.

7. A therapeutic composition as in claim 6, where R is n-pentyl.

8. A therapeutic composition as in claim 6 where R in nonyl.

9. A therapeutic composition as in claim 6 where R is 2,6-dimethyl-2,6- heptadienyl.

10. A therapeutic composition as in claim 8 where $R_1$, $R_2$ & $R_5$ are hydrogen and $R_6$ is chloromethyl.

11. A therapeutic composition as in claim 8 where $R_1$, $R_2$ & $R_5$ are hydrogen and $R_6$ is hydroxymethyl.

12. A therapeutic article suitable for enhancing the transdermal administration to humans and animals of a physiologically active agent comprising a substrate and pharmaceutically acceptable 1,3- dioxacyclopentane or 1,3- dioxacyclohexane containing an aliphatic group having 4 to 18 carbon atoms coated on or impregnated in said substrate.

13. A therapeutic article as defined in claim 12 wherein the substrate is a hydrophilic or hydrophobic film.

14. A therapeutic article as defined in claim 13 wherein the film is a hydrogel.

15. A therapeutic article as defined in claim 13 wherein the film includes a pressure-sensitive adhesive.

16. A method for enhancing the penetration through human and animal skin of a physiologically active agent which comprises post treating the skin with a pharmaceutically acceptable 1,3- dioxacylopentane or 1,3- dioxacylohexane containing at least one $C_4$ to $C_{18}$ aliphatic group.

17. A method for enhancing the penetration through human skin of a physiologically active agent which comprises applying to the skin a composition as defined in claim 1.

* * * * *